(12) United States Patent
Chen et al.

(10) Patent No.: US 12,117,026 B2
(45) Date of Patent: Oct. 15, 2024

(54) ELASTIC CONNECTING ELEMENT, PROCESSING METHOD THEREOF AND FLEXIBLE DRILL INCLUDING ELASTIC CONNECTING ELEMENT

(71) Applicant: Guangzhou Aquila Precise Tools Limited, Guangdong (CN)

(72) Inventors: Hao Chen, Guangdong (CN); Shui On Chan, Guangdong (CN); Qingyang Hu, Guangdong (CN); Qiang Deng, Guangdong (CN)

(73) Assignee: GUANGZHOU AQUILA PRECISE TOOLS LIMITED, Guangdong (CN)

( * ) Notice: Subject to any disclaimer, the term of this patent is extended or adjusted under 35 U.S.C. 154(b) by 399 days.

(21) Appl. No.: 17/520,257

(22) Filed: Nov. 5, 2021

(65) Prior Publication Data

US 2022/0145913 A1   May 12, 2022

(30) Foreign Application Priority Data

Nov. 6, 2020 (CN) .......................... 202011231211.8
Nov. 6, 2020 (CN) .......................... 202011231235.3
Nov. 6, 2020 (CN) .......................... 202011233082.6

(51) Int. Cl.
*F16B 1/02* (2006.01)
*B23K 26/38* (2014.01)

(52) U.S. Cl.
CPC ................ *F16B 1/02* (2013.01); *B23K 26/38* (2013.01)

(58) Field of Classification Search
CPC ... F16C 1/02; F16C 1/04; E21B 17/20; A61B 17/1631; A61B 17/1642; A61B 17/7208;
(Continued)

(56) References Cited

U.S. PATENT DOCUMENTS 1,314,600 A * 9/1919 McCaskey ................ F16C 1/06
                                                        464/174
4,600,037 A * 7/1986 Hatten ..................... E21B 17/20
                                                        175/320
(Continued)

FOREIGN PATENT DOCUMENTS

CN    1193899 A    9/1998
CN    1723835 A    1/2006
(Continued)

OTHER PUBLICATIONS

European Search Report for the European Patent Application No. 21206606.2 issued by the European Patent Office on Mar. 23, 2022.
(Continued)

*Primary Examiner* — Daniel J Wiley
(74) *Attorney, Agent, or Firm* — IP & T GROUP LLP

(57) ABSTRACT

An elastic connecting element, a processing method thereof and a flexible drill including the elastic connecting element are provided. The elastic connecting element includes an elastic part and an outer housing sleeved over the elastic part, the outer housing being formed by connecting a plurality of connecting bodies; the connecting body including a main body and convex teeth provided at two ends of the main body; a groove being formed between each two adjacent convex teeth in each connecting body, such that the two adjacent connecting bodies are connected by fitting the convex teeth of one connecting body with the grooves of the other connecting body.

5 Claims, 11 Drawing Sheets

(58) Field of Classification Search
CPC ............ A61B 17/7266; A61B 17/8625; A61B 17/8685; A61B 1/0055
See application file for complete search history.

(56) References Cited

U.S. PATENT DOCUMENTS

| | | | | |
|---|---|---|---|---|
| 4,706,659 | A * | 11/1987 | Matthews | B25G 1/025 464/57 |
| 5,203,595 | A * | 4/1993 | Borzone | B25B 23/0035 285/331 |
| 5,807,241 | A | 9/1998 | Heimberger | |
| 6,168,213 | B1 * | 1/2001 | Muller | E21B 43/116 285/391 |
| 6,921,397 | B2 * | 7/2005 | Corcoran | A61M 25/0054 464/149 |
| 7,105,003 | B2 * | 9/2006 | Hiltebrandt | A61B 17/32002 606/159 |
| 7,168,486 | B2 * | 1/2007 | Hackworth | E21B 17/04 411/419 |
| 8,382,742 | B2 * | 2/2013 | Hermann | A61B 17/1631 606/1 |
| 9,482,260 | B1 * | 11/2016 | Krause | A61B 17/869 |
| 9,757,536 | B2 * | 9/2017 | Abt | B29C 70/766 |
| 9,801,663 | B2 * | 10/2017 | Krause | A61F 2/44 |
| 9,826,985 | B2 * | 11/2017 | Slobitker | A61B 17/1631 |
| 10,118,015 | B2 * | 11/2018 | de la Rama | A61M 25/0052 |
| 10,524,805 | B2 * | 1/2020 | Zilberman | A61B 17/1642 |
| 10,525,231 | B2 * | 1/2020 | Moquin | A61B 17/22 |
| 11,013,520 | B2 * | 5/2021 | Gareiss | A61B 17/1659 |
| 11,832,856 | B2 * | 12/2023 | Meek | A61B 17/742 |
| 2003/0187449 | A1 * | 10/2003 | McCleary | A61B 17/1668 606/80 |
| 2008/0287951 | A1 * | 11/2008 | Stoneburner | A61B 5/107 606/62 |
| 2010/0151161 | A1 * | 6/2010 | Da Rolo | F16C 1/04 428/34.1 |
| 2011/0158744 | A1 * | 6/2011 | Dornfeld | F16D 1/076 403/364 |
| 2012/0203231 | A1 | 8/2012 | Long et al. | |
| 2013/0090690 | A1 * | 4/2013 | Walsh | A61B 17/7023 606/260 |
| 2013/0230352 | A1 * | 9/2013 | Goulet | F16D 1/02 403/364 |
| 2018/0092681 | A1 * | 4/2018 | Lutz | A61B 17/8685 |
| 2019/0120282 | A1 | 4/2019 | Krause | |
| 2020/0054372 | A1 * | 2/2020 | Stinson | A61B 17/8625 |
| 2021/0386465 | A1 * | 12/2021 | Thaler | A61B 17/7208 |

FOREIGN PATENT DOCUMENTS

| | | |
|---|---|---|
| CN | 107520273 A | 12/2017 |
| CN | 109497914 A | 3/2019 |
| CN | 109497915 A | 3/2019 |
| CN | 109528149 A | 3/2019 |
| CN | 209984177 U | 1/2020 |
| CN | 111110172 A | 5/2020 |
| DE | 10113713 C1 | 12/2002 |
| EP | 1604607 A1 | 12/2005 |
| WO | 9703611 A1 | 2/1997 |
| WO | 9816752 A1 | 4/1998 |

OTHER PUBLICATIONS

Notification to Grant Patent Right for Invention for the Chinese Patent Application No. 202011233082.6 issued by the Chinese Patent Office on Nov. 1, 2022.

Office Action for the European Patent Application No. 21206606.2 issued by the European Patent Office on Apr. 4, 2022.

Office Action for the Chinese Patent Application No. 202011233082.6 issued by the Chinese Patent Office on Jun. 8, 2022 and First Search Result therefor.

* cited by examiner

ELASTIC CONNECTING ELEMENT, PROCESSING METHOD THEREOF AND FLEXIBLE DRILL INCLUDING ELASTIC CONNECTING ELEMENT

CROSS-REFERENCE TO RELATED APPLICATION

The present disclosure claims the priority to the Chinese patent application with the filing No. 202011231211.8, filed on Nov. 6, 2020 with the Chinese Patent Office, and entitled "Elastic Connecting Element", the Chinese patent application with the filing No. 202011233082.6, filed on Nov. 6, 2020 with the Chinese Patent Office, and entitled "Processing method of an elastic connecting element", and the Chinese patent application with the filing No. 202011231235.3, filed on Nov. 6, 2020 with the Chinese Patent Office, and entitled "Flexible Drill", the contents of which are incorporated by reference herein in entirety.

TECHNICAL FIELD

The present disclosure relates to an elastic connecting element, a processing method thereof and a flexible drill including the elastic connecting element.

BACKGROUND ART

An elastic connecting element is often necessary to be used in living and production, and usually has a flexible connection function, and in some products, the elastic connecting element is required to have both the flexible connection function and a function of transmitting an acting force after stressed and bent. Usually, the existing elastic connecting element includes an outer hose and an inner flexible shaft core, and has an insufficient strength, wherein a bending degree is often unable to be well controlled, such that the acting force is unable to be well transmitted. For some products of which the bending degree (angle) is required to be precisely controlled in use, a use effect is often less ideal.

For example, during artificial total hip joint replacement, an artificial total hip joint is composed of an artificial acetabular cup and an artificial femoral head, and the hip joint replacement operation is an operation used for replacing the human hip joint with the artificial hip joint, and specifically is a process of mounting the artificial acetabular cup in the human acetabular fossa and mounting the artificial femoral head in the human femur. When the artificial acetabular cup is mounted in the human acetabular fossa, the acetabular fossa and the acetabular cup are fixed by a screw, a hole is required to be drilled in the acetabular fossa before the screw is screwed, and the drilling action is necessary to be finished by a flexible drill. The flexible drill includes a head (drill bit section) at a front end, a flexible shaft (spring section) in a middle and a handle (transmission section) at a rear end, the spring section in the middle of the existing flexible drill is quite dense, and besides the above-mentioned problem, a large quantity of meat scraps and watery blood adhere to an interior and an exterior of the flexible shaft after use, such that the flexible shaft is not easy to clean and sterilize, and the flexible drill may only be used as a disposable instrument, resulting in resource waste and a diseconomy.

Based on this, it is necessary to provide an elastic connecting element with a high strength and a controllable bending degree.

SUMMARY

On the one hand, an object of the present disclosure is to provide an elastic connecting element and a processing method thereof, which solve defects that an elastic connecting element in the prior art has a low strength and a bending degree and is not easy to control. On the other hand, the present disclosure further provides a flexible drill, which solves the defect that the flexible shaft in a flexible drill in the prior art is not easy to clean.

In a first aspect, the present disclosure provides an elastic connecting element, and the technical solution is as follows.

An elastic connecting element includes an elastic part and an outer housing sleeved over the elastic part, the outer housing being formed by connecting a plurality of connecting bodies; the connecting body including a main body and convex teeth provided at two ends of the main body; a groove being formed between each two adjacent convex teeth in each connecting body, such that the two adjacent connecting bodies are connected by fitting the convex teeth of one of the connecting bodies with the grooves of the other connecting body.

In some embodiments of the present disclosure, each convex tooth includes a connecting portion and at least one protrusion portion; and the connecting portion has one end connected with the main body of the connecting body, and the other end connected with the at least one protrusion portion.

Further, the convex tooth has two protrusion portions, and the two protrusion portions are arranged on two side walls of an end portion of the connecting portion respectively. Such an arrangement makes the convex tooth similar to a T shape, resulting in a simple structure.

In the present disclosure, the convex teeth at the same end portion of the main body of the connecting body are arranged uniformly, and the convex teeth at different end portions are symmetrically arranged at two ends of the main body. The convex teeth are arranged uniformly, such that different convex teeth of the connecting body are stressed the same, and the elastic connecting element is bent in different directions by same deflecting angles.

The present disclosure may be improved in that the main body of the connecting body is a cylinder, and an outer wall and an inner wall of the convex tooth of the connecting body are located on cylindrical surfaces of an outer cylinder and an inner cylinder where the cylinder of the main body is located. With such an arrangement, the whole outer housing is cylindrical after the connection of the connecting body, and may be bent in any direction.

Further, two side walls of the connecting portion of the convex tooth are arranged in a radial direction of the cylinder of the main body; a side wall of the protrusion portion of the convex tooth is provided in the radial direction of the cylinder of the main body. An overall formed by combining the connecting body with the side walls of the connecting portion and the protrusion portion of the convex tooth which are provided radially is cylindrical, and a limiting function is achieved between the convex teeth of adjacent connecting bodies, such that the connecting bodies are connected with each other more firmly.

Further, joints between the side wall of the protrusion portion of the convex tooth and a top surface of the protrusion portion and between the side wall of the protrusion portion and a bottom surface of the protrusion portion are rounded, thus increasing an area of a local slit at contact portions of the convex teeth, improving a permeability, and better facilitating cleanliness of the connecting element.

The present disclosure may be further improved in that a height of the protrusion portion of the convex tooth is less than a depth of the groove formed between two adjacent convex teeth. With such an arrangement, two adjacent connecting elements are firmly connected with each other by the fitness between the convex tooth and the groove, and meanwhile, the depth of the groove may be adjusted to control a radially bent angle between the two adjacent connecting elements.

Further, the depth is set to be 1.5-2.0 times the height of the protrusion portion of the convex tooth.

The present disclosure may be further improved in that end heads are further provided at two ends of the outer housing, and the end head is provided with convex teeth same as the connecting body, and connected with the outer housing by fitness between the convex teeth and the grooves of the connecting body.

In some embodiments of the present disclosure, two ends of the elastic part are fixed to the end heads respectively.

Further, the elastic part is a spring.

In a second aspect, the present disclosure provides a processing method of an elastic connecting element, and an adopted technical solution is as follows.

A processing method of an elastic connecting element includes:

S1: fixing a circular tube on a workbench, and cutting the circular tube by a laser to obtain a housing; and S2: placing an elastic part in the housing, and fixedly connecting the elastic part with two ends of an outer housing to obtain the elastic connecting element.

In the present disclosure, the housing includes the outer housing as mentioned above and end heads arranged at the two ends of the outer housing.

In the present disclosure, the cutting the circular tube by a laser to obtain a housing specifically includes following processes of:

(1) cutting for the end surface of the end head of the housing; and (2) cutting for a matching slit between each convex tooth and a corresponding groove.

The present disclosure may be improved in that the laser cutting process of the matching slit between each convex tooth and the corresponding groove involves a first laser track and a second laser track.

Further, a starting point and an ending point of the first laser track are set in a region between a top of a first convex tooth (any convex tooth) of a connecting body and a bottom of a groove of a connecting body adjacent to the connecting body, with the groove corresponding to the first convex tooth; after entering a first laser-contact incoming point at the top of the first convex tooth from the starting point, the first laser track runs to a top of a last convex tooth sequentially along edges of the convex teeth and the grooves of the connecting body, then enters a bottom of a groove of the adjacent connecting body matched with the last convex tooth, runs to a first laser-contact outgoing point at the bottom of the groove matched with the first convex tooth along edges of the grooves and the convex teeth of the adjacent connecting body, and then reaches the ending point.

Preferably, the starting point and the ending point of the first laser track are a same point; and the first laser track is a closed track.

The first laser-contact incoming point and the first laser-contact outgoing point are points corresponding to the first convex tooth and the groove matched with the first convex tooth.

Further, a starting point and an ending point of the second laser track are located in a same region as the starting point and the ending point of the first laser track; after entering a second laser-contact incoming point at the top of the first convex tooth from the starting point, the second laser track runs to the first laser-contact incoming point along an edge of the top of the first convex tooth, then enters the first laser-contact outgoing point of the adjacent connecting body, runs to a second laser-contact outgoing point at the bottom of the groove matched with the first convex tooth along the bottom, and then reaches the ending point.

Further, the second laser-contact incoming point and the second laser-contact outgoing point are points corresponding to the first convex tooth and the groove matched with the first convex tooth.

Preferably, the starting point and the ending point of the second laser track are different points, the starting point and the ending point of the second laser track are located at two sides of a connecting line of the second laser-contact outgoing point and the second laser-contact incoming point, and the second laser track is a non-closed track.

In the present disclosure, in the laser cutting process, laser energy is 420-470 W, a laser frequency is 4000-8000 Hz, and a laser pulse width is 20-30 μs.

According to one embodiment of the present disclosure, inert protective gas is introduced to a cutting point in the laser cutting process.

Further, the inert protective gas is nitrogen gas.

According to one embodiment of the present disclosure, oxygen is introduced to the cutting point in the laser cutting process. A laser cutting efficiency may be improved by introducing the oxygen.

The present disclosure may be further improved in that water is introduced into the circular tube in the laser cutting process. The water is introduced to cool the circular tube, so as to guarantee a laser cutting effect.

In the present disclosure, the elastic part is a spring.

In a third aspect, the present disclosure provides a flexible drill, and an adopted technical solution is as follows.

A flexible drill includes a head, a flexible shaft and a handle, the flexible shaft having one end connected with the head and the other end connected with the handle, wherein the flexible shaft including an elastic part and a casing sleeved over the elastic part; the casing includes an outer housing and end heads connected to two ends of the outer housing; the casing is connected with the head by one end head and connected with the handle by the other end head; and the outer housing has a specific structure of the outer housing as mentioned before.

The present disclosure may be further improved in that the end head is provided with convex teeth same as the connecting body, and connected with the outer housing by fitness between the convex tooth and a groove of the connecting body.

In some embodiments of the present disclosure, two ends of the elastic part are fixed to the end heads respectively.

Further, the elastic part is a spring.

The present disclosure may be improved in that the handle is hollow, and an interior of the handle is communicated with an interior of the flexible shaft.

The present disclosure has the following beneficial effects.

(1) The outer housing of the elastic connecting element according to the present disclosure is formed by connecting the connecting bodies, the adjacent connecting bodies are connected by fitting the convex teeth with the grooves, the fitness between the convex teeth and the grooves may guarantee a bending function of the elastic connecting element, and meanwhile, a certain limiting function is achieved by the fitness between the convex teeth and the grooves, such that a range of the bending degree of the elastic connecting element may be controlled, thereby better transmitting an acting force. Thus, a material with higher strength may be selected without affecting a connecting function of the elastic connecting element.

(2) In the present disclosure, the convex teeth on the same end of the main body of the connecting body are arranged uniformly, and the convex teeth on different ends are symmetrically arranged at the two ends of the main body, such that the convex teeth is stressed uniformly, and the acting force is better transmitted.

(3) The main body of the connecting body of the elastic connecting element according to the present disclosure is a cylinder, the outer wall and the inner wall of the convex tooth of the connecting body are located on the cylindrical surfaces of the outer cylinder and the inner cylinder where the cylinder of the main body is located, and the two side walls of the connecting portion of the convex tooth are arranged in the radial direction of the cylinder of the main body; the side wall of the protrusion portion of the convex tooth is provided in the radial direction of the cylinder of the main body, such that the connecting bodies are connected firmly, and stressed uniformly, and the elastic connecting element may be bent by 360 degrees.

(4) In the processing method of an elastic connecting element according to the present disclosure, the circular tube is cut using a laser cutting technology, so as to obtain the elastic connecting element with a high strength and a controllable bending degree after a processing operation. The elastic connecting element according to the present application is difficult to machine using an existing common machining technology, and the method according to the present disclosure improves a product quality and a manufacturing efficiency, and reduces a cost.

(5) In the laser cutting process in the present disclosure, a laser cutting path is optimized, and the first laser track and the second laser track are adopted, which may avoid appearance of scorching point(s) at an edge of the elastic connecting body in an initial laser cutting process and an adverse effect of a stress generated by a point effect on a mechanical property of a product, thereby guaranteeing the quality of the product; meanwhile, it shortens a laser closing gap time in the cutting process for a single slit and a laser closing gap time of movement from the matching slit between one convex tooth and groove to the matching slit between another convex tooth and groove, thus further improving the laser cutting efficiency, and reducing the cost.

(6) The flexible shaft of the flexible drill according to the present disclosure is formed by connecting the plurality of connecting bodies by means of the convex teeth and the grooves, and in such a connecting mode more slits are present, such that the flexible shaft is convenient to clean, and may be repeatedly utilized after sterilized, thus saving resources.

BRIEF DESCRIPTION OF DRAWINGS

The present disclosure will be described in further detail with reference to the following drawings and specific embodiments.

Figure 1:
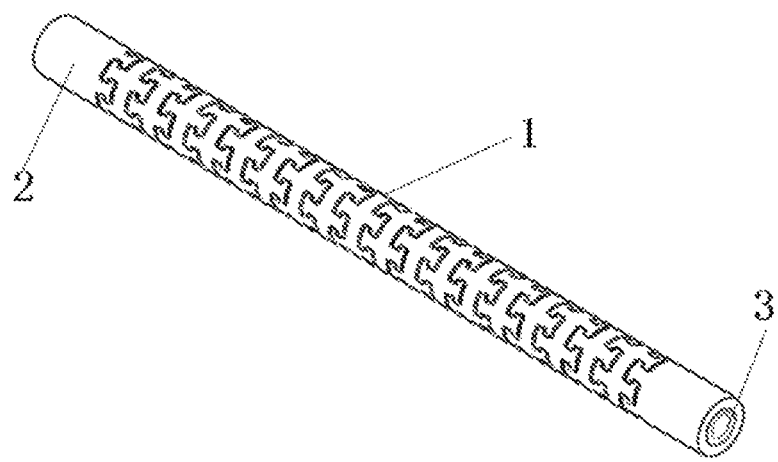
FIG. 1 is a schematic diagram of an overall structure of an elastic connecting element according to the present disclosure.

Reference numerals: 1: outer housing; 2: end head; 3: elastic part; 4: connecting body; 5: first laser track; 6: second laser track; 7: section track; 8: head; 9: flexible shaft; 10: handle; 401: main body; 402: convex tooth; 4021: connecting portion; 4022: protrusion portion; 501: first starting point; 502: first laser-contact incoming point; 503: first laser-contact outgoing point; 504: first ending point; 601: second starting point; 602: second laser-contact incoming point; 603: second laser-contact outgoing point; 604: second ending point.

DETAILED DESCRIPTION

First Embodiment

Figure 2:
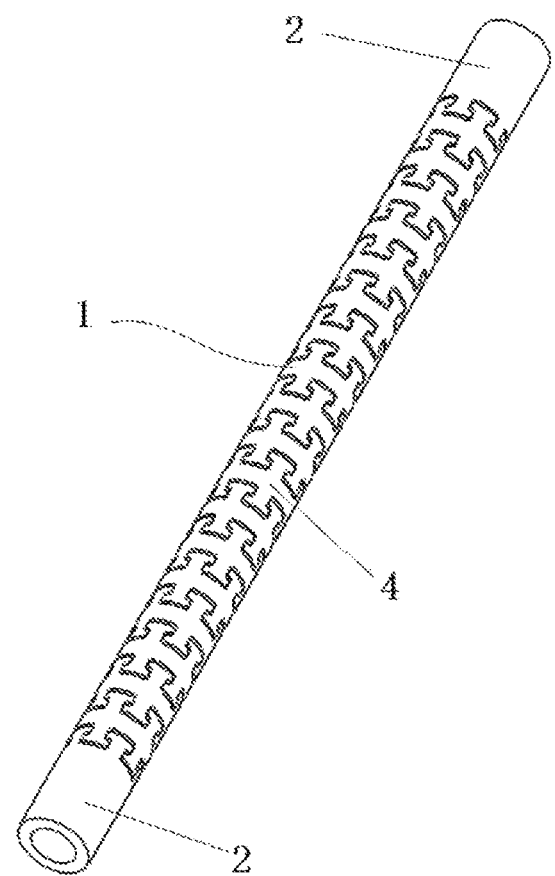
FIG. 2 is a schematic structural diagram of a casing of the elastic connecting element according to the present disclosure.
Figure 3:
FIG. 3 is an exploded view of FIG. 2.
Figure 4:
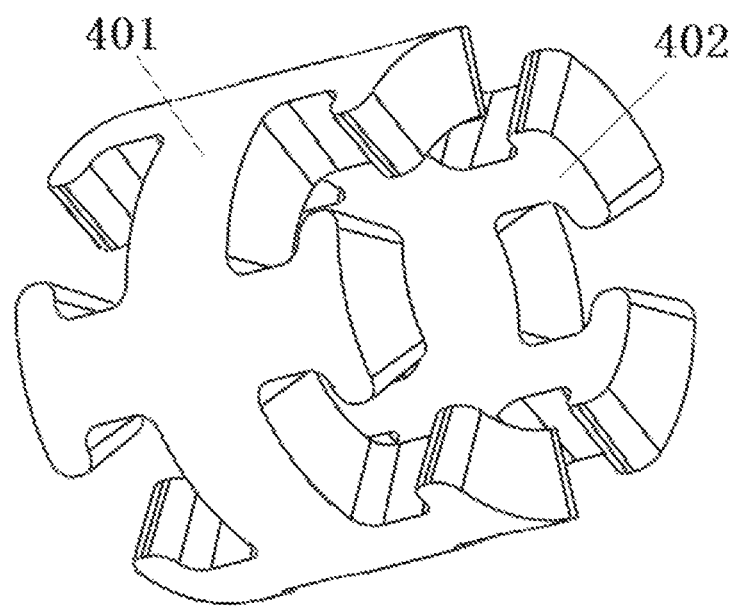
FIG. 4 is a schematic diagram of an overall structure of a connecting body according to the present disclosure.
Figure 5:
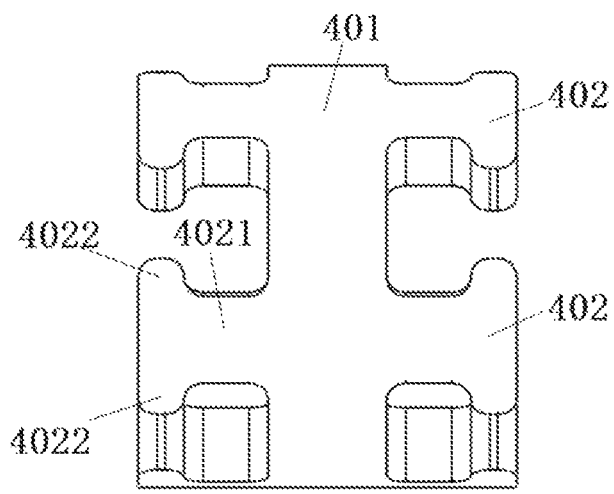
FIG. 5 is a front view of the connecting body according to the present disclosure.
Figure 6:
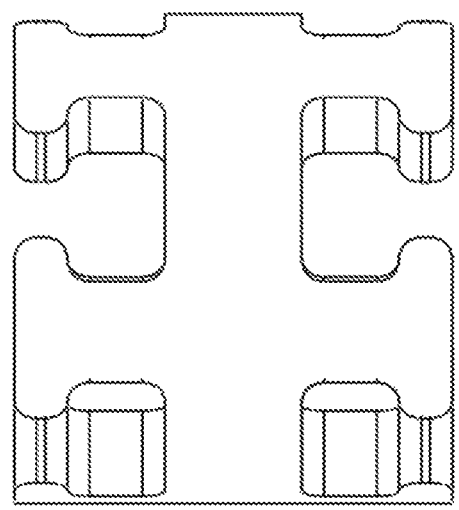
FIG. 6 is a rear view of the connecting body according to the present disclosure.
Figure 7:
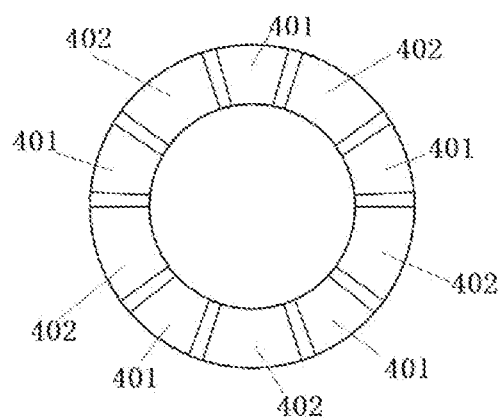
FIG. 7 is a left view of the connecting body according to the present disclosure.
Figure 8:
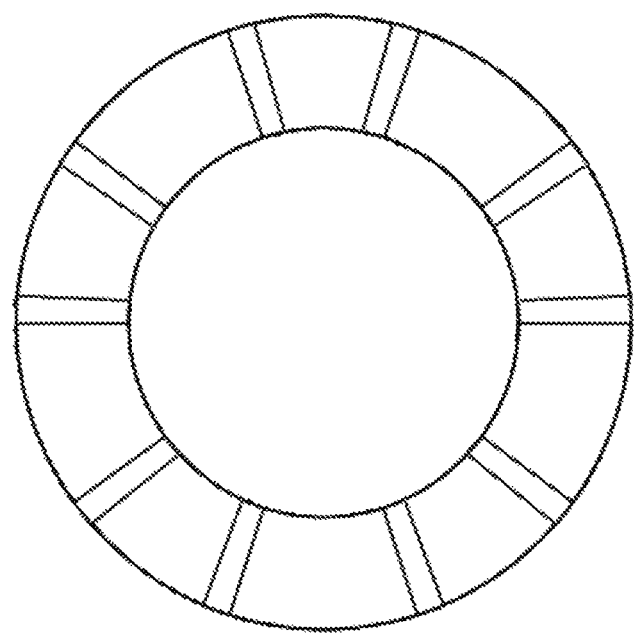
FIG. 8 is a right view of the connecting body according to the present disclosure.
Figure 9:
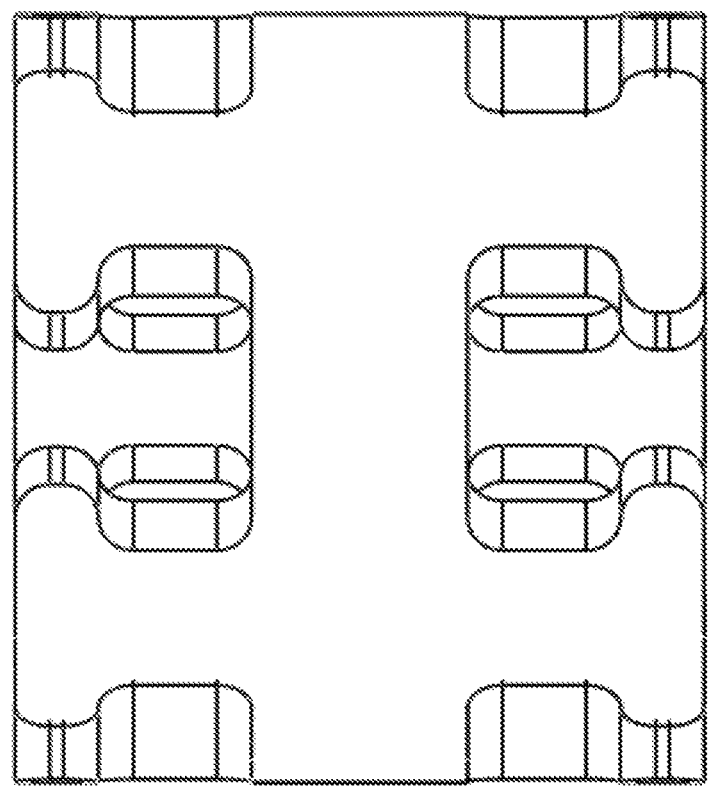
FIG. 9 is a top view of the connecting body according to the present disclosure.
Figure 10:
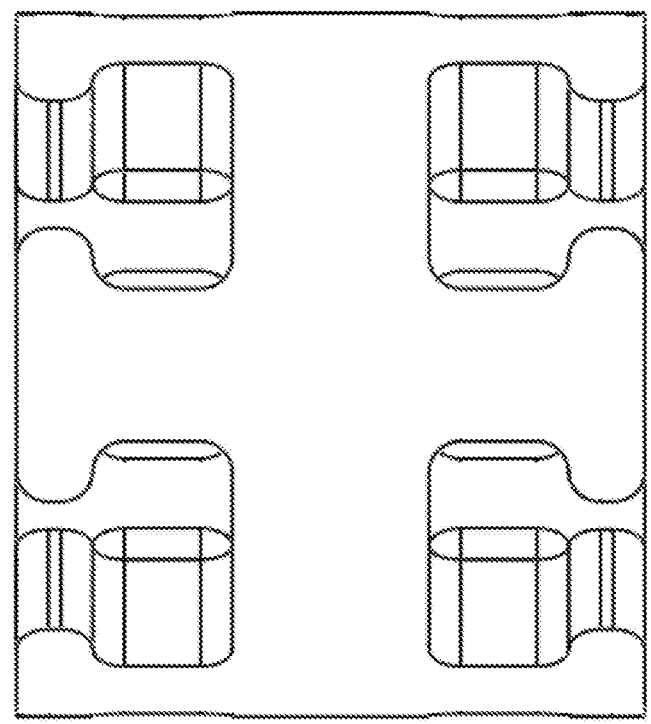
FIG. 10 is a bottom view of the connecting body according to the present disclosure.
Figure 11:
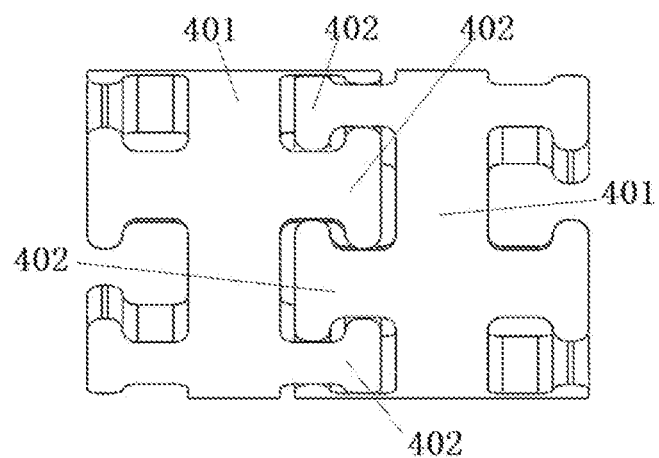
FIG. 11 is a schematic diagram of a connection structure of two connecting bodies.
Figure 12:
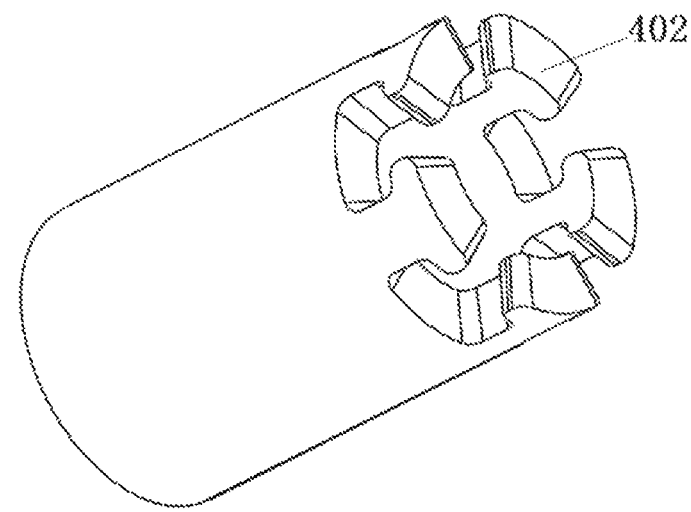
FIG. 12 is a schematic structural diagram of an end head according to the present disclosure.
Figure 13:
FIG. 13 is a front view of the end head according to the present disclosure.
Figure 14:
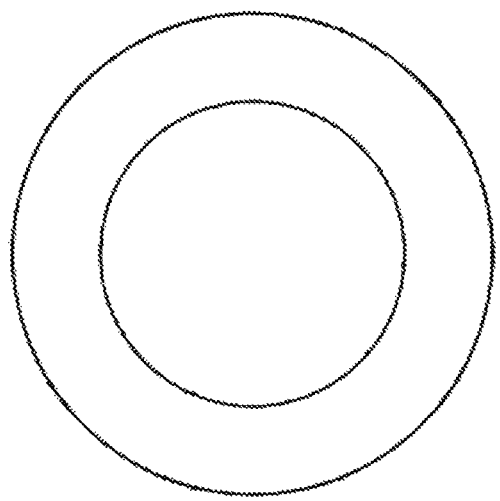
FIG. 14 is a left view of the end head according to the present disclosure.
Figure 15:
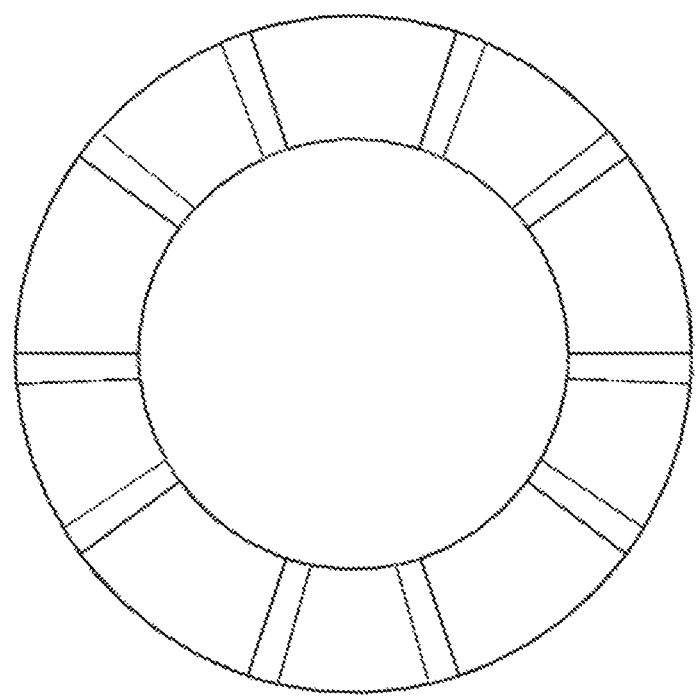
FIG. 15 is a right view of the end head according to the present disclosure.

As shown in FIGS. 1 to 15, an elastic connecting element includes a casing and an elastic part 3. The casing includes an outer housing 1 and end heads 2. The outer housing 1 is sleeved over the elastic part 3, and the two end heads 2 are connected with two ends of the outer housing 1 respectively.

The outer housing 1 is formed by connecting a plurality of connecting bodies 4 in sequence. Each connecting body 4 includes a main body 401 and convex teeth 402 provided at two ends of the main body 401; the convex teeth 402 on a same end portion of the main body 401 of the connecting body 4 are arranged uniformly, a groove is formed between each two adjacent convex teeth 402, and the convex teeth 402 on different end portions are symmetrically arranged at the two ends of the main body 401. In the present embodiment, the main body 401 of the connecting body 4 is a cylinder, and an outer wall and an inner wall of the convex tooth 402 of the connecting body 4 are located on cylindrical surfaces of an outer cylinder and an inner cylinder where the cylinder of the main body 401 is located. Five convex teeth 402 are uniformly arranged at each of the two ends of each connecting body 4. The convex tooth 402 includes a connecting portion 4021 and two protrusion portions 4022; one end of the connecting portion 4021 is connected with the main body 401 of the connecting body 4, and the other end of the connecting portion 4021 is connected with the protrusion portions 4022, and the two protrusion portions 4022 are arranged on two side walls of an end portion of the connecting portion 4021 respectively. Two side walls of the connecting portion 4021 of the convex tooth 402 are arranged in a radial direction of the cylinder of the main body 401; a side wall of the protrusion portion 4022 of the convex tooth 402 is provided in the radial direction of the cylinder of the main body 401, and joints between the side wall of the protrusion portion 4022 and a top surface and between the side wall of the protrusion portion and a bottom surface are rounded. A height of the protrusion portion 4022 of the convex tooth 402 is less than a depth of the groove formed between two adjacent convex teeth 402, and in the present embodiment, the depth of the groove is set to be 1.8 times the height of the protrusion portion 4022 of the convex tooth 402. With the above-mentioned arrangement, two adjacent connecting bodies 4 are connected with each other by fitting the convex teeth 402 of one connecting body 4 with the grooves of the other connecting body 4.

The end head 2 is cylindrical and has one end provided with convex teeth 402 same as the connecting body 4. The two end heads 2 are connected with the outer housing 1 by fitness between the convex teeth 402 of the end heads 2 and the grooves of the two outermost connecting bodies 4 of the outer housing 1. Two ends of the elastic part 3 are fixed to the two end heads 2 respectively, and in the present embodiment, the elastic part 3 is a spring.

Second Embodiment

The present embodiment is different from the first embodiment in that two elastic parts 3 are arranged inside the outer housing 1, the innermost elastic part is a spring, the middle elastic part is a spring, and the innermost spring is placed inside the middle spring. Two ends of both the innermost spring and the middle spring are fixed to the end heads 2 respectively.

Third Embodiment

A processing method of the elastic connecting element according to the first embodiment includes the following steps:

S1: fixing a stainless-steel circular tube with an outer tube diameter of 5.5 mm and a tube thickness of 1 mm on a workbench, and cutting the circular tube by a laser to obtain a housing.

The specific process is as follows.

Figure 16:
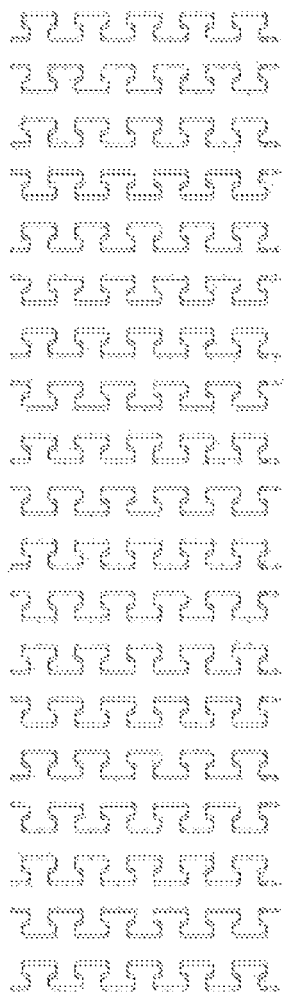
FIG. 16 is a schematic diagram of a laser cutting pattern.
Figure 17:
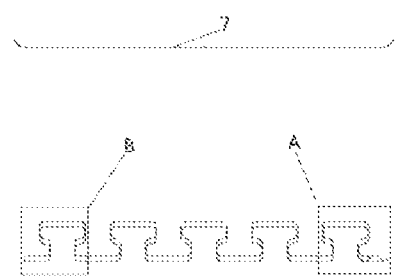
FIG. 17 is a schematic diagram of laser cutting for a matching slit between one convex tooth and a groove.
Figure 18:
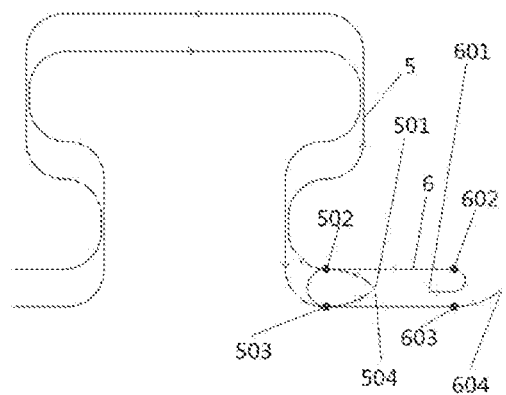
FIG. 18 is an enlarged view of portion A of FIG. 17.
Figure 19:
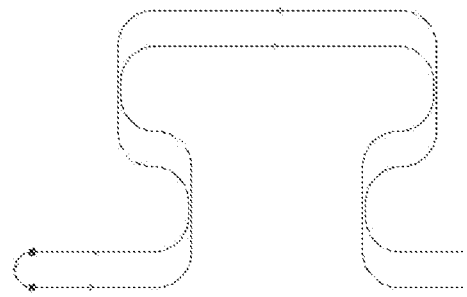
FIG. 19 is an enlarged view of portion B of FIG. 17.
Figure 20:
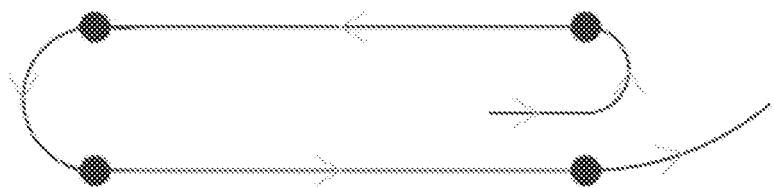
FIG. 20 is a schematic diagram of a second laser track.

(1) A processing pattern file and track files are set: an end surface track 7, a first laser track 5 and a second laser track 6, referring to FIGS. 16 to 20.

The first laser track 5 is a closed track, and a first starting point 501 and a first ending point 504 are a same point. The first starting point 501 and the first ending point 504 of the first laser track 5 are set in a region between a top of a first convex tooth (any convex tooth) of a connecting body 4 and a bottom of a groove of a connecting body adjacent to the connecting body 4, with the groove corresponding to the first convex tooth; the first laser track 5 enters a first laser-contact incoming point 502 at the top of the first convex tooth from the first starting point 501, wherein in the present embodiment, the first laser-contact incoming point 502 is a joint between a top surface and a rounded arc surface of a protrusion portion 4022 of a convex tooth 402; then runs to a middle point of a top of a last convex tooth 402 sequentially along edges of the convex teeth 402 and the grooves of the connecting body 4; then enters a middle point of a bottom of a matched groove of the adjacent connecting body 4; runs to a first laser-contact outgoing point 503 at the bottom of the groove matched with the first convex tooth along edges of the grooves and the convex teeth 402 of the adjacent connecting body 4, wherein in the present embodiment, the first laser-contact outgoing point 503 is a point of the bottom of the groove corresponding to the first laser-contact incoming point 502; and then reaches the first ending point 504.

A second starting point 601 and a second ending point 604 of the second laser track 6 are located in a same region as the first starting point 501 and the first ending point 504 of the first laser track 5; after entering a second laser-contact incoming point 602 at the top of the first convex tooth from the second starting point 601, the second laser track 6 runs to the first laser-contact incoming point 502 along an edge of the top of the first convex tooth, wherein in the present embodiment, the second laser-contact incoming point 602 is a middle point of the top of the first convex tooth; then enters the first laser-contact outgoing point 503 of the adjacent connecting body 4; runs to a second laser-contact outgoing point 603 at the bottom of the groove matched with the first convex tooth 402 along the edge of the bottom of the groove, wherein in the present embodiment, the second laser-contact outgoing point 603 is a point of the bottom of the groove corresponding to the second laser-contact incoming point 602; and then reaches the second ending point 604. In the present embodiment, the second starting point 601 and the second ending point 604 of the second laser track 6 are different points, the second starting point 601 and the second ending point 604 of the second laser track 6 are located on two sides of a connecting line of the second laser-contact outgoing point 603 and the second laser-contact incoming point 602, and the second laser track 6 is a non-closed track.

Laser cutting parameters are set, in which laser energy is 440 W, a laser frequency is 5500 Hz, a laser pulse width is 25 µs, an IO trigger delay is 0 ms, a delay after the laser is emitted is 80 ms, a delay after the laser is stopped is 0 ms, and a delay before the laser is stopped is 0 ms; the circular tube is axially moved and rotated in the processing process, a laser emitting device is not moved, and motion parameters include a linear speed of 8 mm/s, and an arc speed of 8 mm/s. A platform is PlatformI, wet cutting is TRUE, and a focal length is −0.1 mm (0 mm represents a positive focal length).

(2) The laser is emitted to radially cut the stainless-steel circular tube to obtain a first end surface of the housing, and the laser is stopped.

(3) The laser emitting device is moved to the first starting point 501 of the first laser track 5, the laser is emitted to cut the circular tube along the first laser track 5, and completes the cutting when reaching the first ending point 504 of the first laser track 5, and the laser is stopped; then, the laser emitting device is moved from the first ending point 504 of the first track to the second starting point 601 of the second laser track 6, the laser is emitted to cut the circular tube along the second laser track 6, and completes the cutting when reaching the ending point of the second laser track 6, and the laser is stopped, completing the cutting for the matching slit between the first convex tooth and the groove. Then, the laser emitting device is moved from the ending point of the second laser track 6 to the first starting point 501 of a next first laser track 5, and starts to perform cutting for the matching slit between a second convex tooth and a groove, and completing the cutting for the matching slit between the second convex tooth and the groove after moving along one first laser track 5 and one second laser track 6, and the process is repeated until completing the matching slits between all the convex teeth and the grooves.

(4) The laser is emitted to radially cut the stainless-steel circular tube to obtain a second end surface of the housing, the laser is stopped, and a machining process of the housing is completed.

S2: A spring is placed in the housing, and fixedly connected with two ends of an outer housing to obtain the finished elastic connecting element.

Fourth Embodiment

Figure 21:
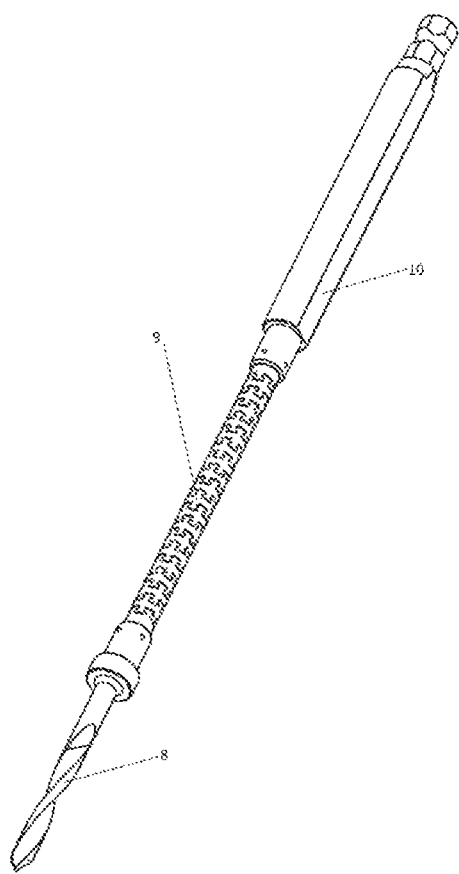
FIG. 21 is a schematic diagram of an overall structure of a flexible drill according to the present disclosure.

As shown in FIGS. 1 to 16 and 21, a flexible drill includes a head 8, a flexible shaft 9 and a handle 10.

The flexible shaft 9 includes a casing and an elastic part 3, and the casing is sleeved over the elastic part 3. The casing includes an outer housing 1 and end heads 2. The two end heads 2 are connected with two ends of the outer housing 1 respectively.

The outer housing 1 is formed by connecting a plurality of connecting bodies 4 in sequence. Each connecting body 4 includes a main body 401 and convex teeth 402 provided at two ends of the main body 401; the convex teeth 402 on a same end portion of the main body 401 of the connecting body 4 are arranged uniformly, a groove is formed between each two adjacent convex teeth 402, and the convex teeth 402 on different end portions are symmetrically arranged at the two ends of the main body 401. In the present embodiment, the main body 401 of the connecting body 4 is a cylinder, and an outer wall and an inner wall of the convex tooth 402 of the connecting body 4 are located on cylindrical surfaces of an outer cylinder and an inner cylinder where the cylinder of the main body 401 is located. Five convex teeth 402 are uniformly arranged at each of the two ends of each connecting body 4. The convex tooth 402 includes a connecting portion 4021 and two protrusion portions 4022; one end of the connecting portion 4021 is connected with the main body 401 of the connecting body 4, and the other end of the connecting portion 4021 is connected with the protrusion portion 4022, and the two protrusion portions 4022 are arranged on two side walls of an end portion of the connecting portion 4021 respectively. Two side walls of the connecting portion 4021 of the convex tooth 402 are arranged in a radial direction of the cylinder of the main body 401; a side wall of the protrusion portion 4022 of the convex tooth 402 is provided in the radial direction of the cylinder of the main body 401, and joints between the side wall of the protrusion portion 4022 and a top surface and between the side wall of the protrusion portion and a bottom surface are rounded. A height of the protrusion portion 4022 of the convex tooth 402 is less than a depth of the groove formed between two adjacent convex teeth 402, and in the present embodiment, the depth of the groove is set to be 1.8 times the height of the protrusion portion 4022 of the convex tooth 402. With the above-mentioned arrangement, two adjacent connecting bodies 4 are connected with each other by fitting the convex teeth 402 of one connecting body 4 with the grooves of the other connecting body 4. The end head 2 is cylindrical and has one end provided with convex teeth 402 same as the connecting body 4. The two end heads 2 are connected with the outer housing 1 by fitness between the convex teeth 402 of the end heads 2 and the grooves of the two outermost connecting bodies 4 of the outer housing 1. Two ends of the elastic part 3 are fixed to the two end heads 2 respectively, and in the present embodiment, the elastic part 3 is a spring.

The flexible shaft 9 is fixedly connected with the head 8 by one end head 2 and with the handle 10 by the other end head 2.

Fifth Embodiment

Figure 22:
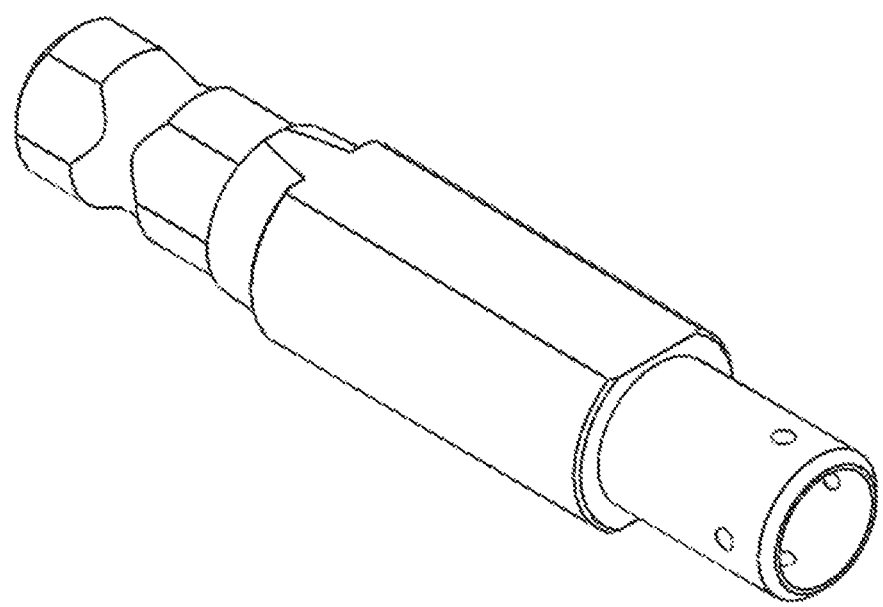
FIG. 22 is a schematic diagram of an overall structure of a handle in the fifth embodiment of the present disclosure.
Figure 23:
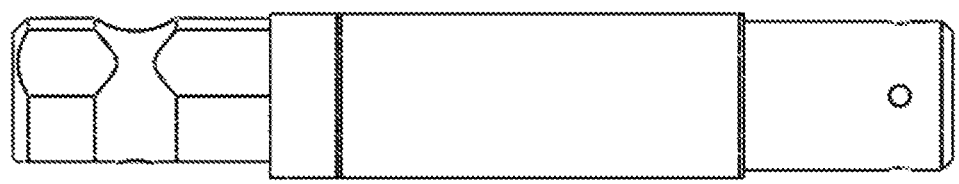
FIG. 23 is a front view of the handle in the fifth embodiment of the present disclosure.
Figure 24:
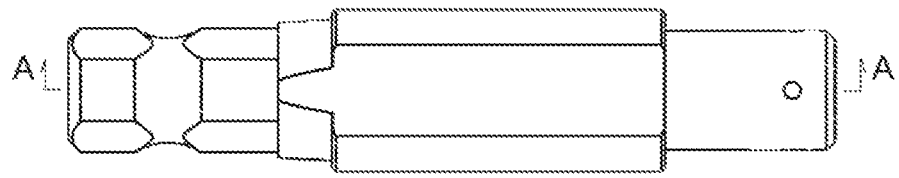
FIG. 24 is a front view of the handle in the fifth embodiment of the present disclosure.
Figure 25:
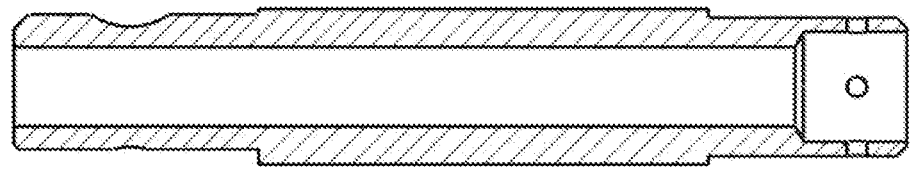
FIG. 25 is a view taken along A-A of FIG. 24.

A flexible drill shown in FIGS. 22 to 25 is different from that in the first embodiment in that the handle 10 of the flexible drill is hollow, and an interior of the handle is communicated with an interior of the flexible shaft 9, such that the interior of the flexible shaft 9 may be washed by injecting water at a tail end of the handle 10, thus achieving a more convenient effect and a better cleaning effect.

The above embodiments of the present disclosure are not intended to limit the scope of the present disclosure, and the embodiments of the present disclosure are not limited thereto; various other modifications, substitutions or alterations made to the above structures of the present disclosure without departing from the basic technical idea of the present disclosure according to the common technical knowledge and common means of the art based on the above-mentioned disclosure of the present disclosure should fall within the scope of the present disclosure.

What is claimed is:

1. A processing method of the elastic connecting element, comprising steps of:
    S1: fixing a circular tube on a workbench, and cutting the circular tube by a laser to obtain a housing,
    wherein the housing comprises the outer housing and end heads arranged at the two ends of the outer housing; and
    S2: placing the elastic part in the housing to make the elastic part fixedly connected with the two ends of the outer housing to obtain the elastic connecting element,
    wherein each of the convex teeth comprises a connecting portion and at least one protrusion portion; and the connecting portion has one end connected with the main body of the connecting body, and the other end connected with the at least one protrusion portion,
    wherein the step of cutting the circular tube by a laser to obtain a housing comprises processes of:
    cutting for an end surface of the end head of the housing; and
    cutting for a matching slit between a convex tooth and a groove,
    wherein the cutting process for a matching slit between the convex tooth and the groove, which is laser cutting, involves a first laser track and a second laser track,
    wherein a starting point and an ending point of the first laser track are set in a region between a top of a first convex tooth of a connecting body and a bottom of a groove of a connecting body adjacent to the connecting body, with the groove corresponding to the first convex tooth; and after entering a first laser-contact incoming point at the top of the first convex tooth from the starting point, the first laser track runs to a top of a last convex tooth sequentially along edges of the convex teeth and the grooves of the connecting body, then enters a bottom of a groove of the adjacent connecting body matched with the last convex tooth, runs to a first laser-contact outgoing point at the bottom of the groove matched with the first convex tooth along edges of the grooves and the convex teeth of the adjacent connecting body, and then reaches the ending point.

2. The processing method of the elastic connecting element according to claim 1,
wherein the starting point and the ending point of the first laser track are a same point; the first laser track is a closed track; and the first laser-contact incoming point and the first laser-contact outgoing point are points corresponding to the first convex tooth and the groove matched with the first convex tooth.

3. The processing method of the elastic connecting element according to claim 1,
wherein a starting point and an ending point of the second laser track are located in a same region as the starting point and the ending point of the first laser track; and after entering a second laser-contact incoming point at the top of the first convex tooth from the starting point, the second laser track runs to the first laser-contact incoming point along an edge of the top of the first convex tooth, then enters the first laser-contact outgoing point of the adjacent connecting body, runs to a second laser-contact outgoing point at the bottom of the groove matched with the first convex tooth along the bottom of the groove, and then reaches the ending point.

4. The processing method of the elastic connecting element according to claim 3,
wherein the second laser-contact incoming point and the second laser-contact outgoing point are points corresponding to the first convex tooth and the groove matched with the first convex tooth; and the starting point and the ending point of the second laser track are different points, the starting point and the ending point of the second laser track are located on two sides of a connecting line of the second laser-contact outgoing point and the second laser-contact incoming point, and the second laser track is a non-closed track.

5. The processing method of the elastic connecting element according to claim 4, wherein in the laser cutting process, laser energy is 420-470 W, a laser frequency is 4000-8000 Hz, and a laser pulse width is 20-30 μs.

* * * * *